(12) United States Patent
Mercier et al.

(10) Patent No.: US 11,419,665 B2
(45) Date of Patent: Aug. 23, 2022

(54) ELECTROSURGICAL FORCEPS

(71) Applicant: Covidien LP, Mansfield, MA (US)

(72) Inventors: Daniel W. Mercier, Erie, CO (US);
Kelley D. Goodman, Erie, CO (US);
Craig V. Krastins, Arvada, CO (US);
Robert F. Mccullough, Jr., Boulder, CO (US); Jennifer L. Rich, Parker, CO (US); Grant T. Sims, Boulder, CO (US)

(73) Assignee: Covidien LP, Mansfield, MA (US)

( * ) Notice: Subject to any disclaimer, the term of this patent is extended or adjusted under 35 U.S.C. 154(b) by 336 days.

(21) Appl. No.: 16/584,297

(22) Filed: Sep. 26, 2019

(65) Prior Publication Data
US 2020/0129224 A1    Apr. 30, 2020

Related U.S. Application Data

(60) Provisional application No. 62/751,016, filed on Oct. 26, 2018.

(51) Int. Cl.
*A61B 18/14*    (2006.01)
*A61B 18/00*    (2006.01)

(52) U.S. Cl.
CPC .. *A61B 18/1442* (2013.01); *A61B 2018/0063* (2013.01); *A61B 2018/00589* (2013.01); *A61B 2018/00595* (2013.01); *A61B 2018/1455* (2013.01)

(58) Field of Classification Search
CPC ...... A61B 18/1442; A61B 2018/00589; A61B 2018/00595; A61B 2018/0063; A61B 2018/1455

USPC ............................ 606/51–52, 169, 205–207
See application file for complete search history.

(56) References Cited

U.S. PATENT DOCUMENTS

| | | |
|---|---|---|
| 5,219,354 A | 6/1993 | Choudhury et al. |
| 5,447,265 A | 9/1995 | Vidal et al. |
| 5,499,997 A | 3/1996 | Sharpe et al. |
| 5,797,938 A | 8/1998 | Paraschac et al. |
| 5,860,975 A | 1/1999 | Goble et al. |
| 6,603,100 B2 | 8/2003 | Wilkins et al. |
| 7,207,472 B2 | 4/2007 | Wukusick et al. |
| 7,297,136 B2 | 11/2007 | Wyrick |
| 7,550,975 B2 | 6/2009 | Honda et al. |

(Continued)

FOREIGN PATENT DOCUMENTS

| | | |
|---|---|---|
| DE | 102010013060 A1 | 9/2011 |
| DE | 202012013219 U1 | 11/2015 |
| WO | 2009153015 A1 | 12/2009 |

*Primary Examiner* — Khadijeh A Vahdat

(57) ABSTRACT

An electrosurgical forceps includes a pair of first and second shaft members pivotably coupled to one another, an end effector assembly coupled to the pair of first and second shaft members, a knife selectively translatable through the first shaft member and the end effector assembly, and a knife deployment mechanism. The second shaft member has a flange extending therefrom toward the first shaft member. The knife deployment mechanism includes a distal extension movably coupled to the first shaft member and configured to engage the flange of the second shaft member when the knife is an extended position and the end effector assembly is in a closed configuration. The engagement between the distal extension and the flange resists movement of the end effector assembly from the closed configuration.

14 Claims, 4 Drawing Sheets

(56) References Cited

U.S. PATENT DOCUMENTS

| | | |
|---|---|---|
| 7,819,299 B2 | 10/2010 | Shelton, IV et al. |
| 8,197,479 B2 | 6/2012 | Olson et al. |
| 8,343,151 B2 | 1/2013 | Siebrecht et al. |
| 8,388,646 B2 | 3/2013 | Chojin |
| 8,480,671 B2 | 7/2013 | Mueller |
| 8,568,412 B2 | 10/2013 | Brandt et al. |
| 8,628,557 B2 | 1/2014 | Collings et al. |
| 8,679,115 B2 | 3/2014 | Reschke |
| 8,696,665 B2 | 4/2014 | Hunt et al. |
| 8,752,264 B2 | 6/2014 | Ackley et al. |
| 8,920,461 B2 | 12/2014 | Unger et al. |
| 8,968,313 B2 | 3/2015 | Larson |
| 8,973,805 B2 | 3/2015 | Scirica et al. |
| 9,345,534 B2 | 5/2016 | Artale et al. |
| 9,610,114 B2 | 4/2017 | Baxter, III et al. |
| 9,675,405 B2 | 6/2017 | Trees et al. |
| 9,707,029 B2 | 7/2017 | Nobis et al. |
| 9,877,775 B2 | 1/2018 | Hart |
| 2001/0045442 A1 | 11/2001 | Whitman |
| 2004/0094597 A1 | 5/2004 | Whitman et al. |
| 2005/0119655 A1* | 6/2005 | Moses ................ A61B 18/1442 606/51 |
| 2007/0043352 A1 | 2/2007 | Garrison et al. |
| 2007/0173814 A1 | 7/2007 | Hixson et al. |
| 2010/0286691 A1 | 11/2010 | Kerr et al. |
| 2011/0054468 A1 | 3/2011 | Dycus |
| 2012/0197253 A1 | 8/2012 | Nishimura et al. |
| 2012/0265241 A1 | 10/2012 | Hart et al. |
| 2013/0296843 A1 | 11/2013 | Boudreaux et al. |
| 2014/0005704 A1 | 1/2014 | Vakharia et al. |
| 2014/0276738 A1 | 9/2014 | Price et al. |
| 2014/0276970 A1 | 9/2014 | Messerly et al. |
| 2014/0309665 A1 | 10/2014 | Parihar et al. |
| 2015/0272660 A1 | 10/2015 | Boudreaux et al. |
| 2016/0135868 A1 | 5/2016 | Joseph et al. |
| 2016/0166256 A1 | 6/2016 | Baxter, III et al. |
| 2017/0196629 A1 | 7/2017 | Nagtegaal |
| 2017/0238991 A1 | 8/2017 | Worrell et al. |
| 2017/0245933 A1 | 8/2017 | Graham et al. |
| 2017/0367752 A1 | 12/2017 | Boudreaux et al. |

* cited by examiner

ELECTROSURGICAL FORCEPS

CROSS REFERENCE TO RELATED APPLICATION

The present application claims the benefit of and priority to U.S. Provisional Application Ser. No. 62/751,016, filed on Oct. 26, 2018 the entire contents of which are incorporated herein by reference.

BACKGROUND

The present disclosure relates to electrosurgical instruments and, more particularly, to electrosurgical forceps for grasping, treating, and/or dividing tissue.

TECHNICAL FIELD

A surgical forceps is a plier-like instrument which relies on mechanical action between its jaws to grasp tissue. Electrosurgical forceps utilize both mechanical clamping action and electrical energy to treat tissue, e.g., coagulate, cauterize, and/or seal tissue.

Typically, once tissue is treated, the surgeon has to accurately sever the treated tissue. Accordingly, many electrosurgical forceps have been designed which incorporate a knife configured to effectively sever tissue after treating the tissue.

SUMMARY

As used herein, the term "distal" refers to the portion that is being described which is further from a surgeon, while the term "proximal" refers to the portion that is being described which is closer to a surgeon. Further, to the extent consistent, any of the aspects described herein may be used in conjunction with any or all of the other aspects described herein.

As used herein, the terms parallel and perpendicular are understood to include relative configurations that are substantially parallel and substantially perpendicular up to about +/−10 degrees from true parallel and true perpendicular.

An electrosurgical forceps provided in accordance with aspects of the present disclosure includes a pair of first and second shaft members pivotably coupled to one another, an end effector assembly coupled to the pair of first and second shaft members, a knife, and a knife deployment mechanism. The second shaft member has a flange extending therefrom toward the first shaft member. The end effector assembly is configured to move between an open configuration and a closed configuration in response to pivoting of the first and second shaft members. The knife is selectively translatable through the first shaft member from a retracted position to an extended position in which the knife extends at least partially through the end effector assembly. The knife deployment mechanism is coupled to the first shaft member and includes a distal extension coupled to the knife. The distal extension is configured to engage the flange of the second shaft member when the knife is in the extended position and the end effector assembly is in the closed configuration. The engagement between the distal extension and the flange resists movement of the end effector assembly from the closed configuration.

In aspects, the knife deployment mechanism may include a linkage operably coupled to the knife configured to move the knife between the retracted and extended positions. The distal extension may be coupled to and extends distally from a distal end portion of the linkage.

In some aspects, the knife deployment mechanism may include a pivot pin rotatably supported by the distal end portion of the linkage and coupled to the knife.

In further aspects, the knife deployment mechanism may include a trigger rotatably coupled to the first shaft member, and a crank having a first end portion coupled to the trigger and a second end portion rotatably coupled to a proximal end portion of the linkage. The knife may be configured to move between the retracted and extended positions in response to an actuation of the trigger.

In other aspects, the crank may rotate in response to an actuation of the trigger to rotate and translate the linkage.

In aspects, the flange may define a hole dimensioned for receipt of the distal extension.

In some aspects, the distal extension may extend through the hole upon the knife moving to the extended position, whereby the hole captures the distal extension and resists the first and second shaft members moving away from one another.

In accordance with an aspect of the present disclosure, an electrosurgical forceps is provided and includes a pair of first and second shaft members pivotably coupled to one another, an end effector assembly coupled to the pair of first and second shaft members, a knife, and a knife deployment mechanism. The second shaft member has a flange extending therefrom toward the first shaft member. The knife is selectively translatable through the first shaft member from a retracted position to an extended position in which the knife extends at least partially through the end effector assembly. The knife deployment mechanism is coupled to the first shaft member and includes a trigger, a linkage, and a distal extension. The trigger extends from the first shaft member and is rotatably coupled to the first shaft member. The knife deployment mechanism further includes a linkage and a distal extension. The linkage is operably coupled to the trigger and a proximal end portion of the knife. The distal extension is coupled to a distal end portion of the linkage and is configured to engage the flange of the second shaft member when the knife is in the extended position. The engagement between the linkage and the flange resists movement of the first and second shaft members away from one another.

In aspects, the knife deployment mechanism may include a crank having a first end portion coupled to the trigger and a second end portion operably coupled to a proximal end portion of the linkage.

In some aspects, the end effector assembly may include a first jaw member coupled to and extending distally from the first shaft member, and a second jaw member coupled to and extending distally from the second shaft member. The first and second jaw members may be configured to move between an open configuration and a closed configuration in response to pivoting of the first and second shaft members.

In further aspects, engagement between the linkage and the flange may resist movement of the first and second jaw members from the closed configuration.

In other aspects, the flange may define a hole dimensioned for receipt of the distal extension.

In aspects, the distal extension may extend through the hole upon the knife moving to the extended position, whereby the hole captures the distal extension and resists the first and second shaft members moving away from one another.

In some aspects, the knife deployment mechanism may include a pivot pin rotatably supported by the distal end portion of the linkage and coupled to the knife.

BRIEF DESCRIPTION OF THE DRAWINGS

Various aspects and features of the present disclosure are described hereinbelow with reference to the drawings wherein like numerals designate identical or corresponding elements in each of the several views.

DETAILED DESCRIPTION

Figure 1:
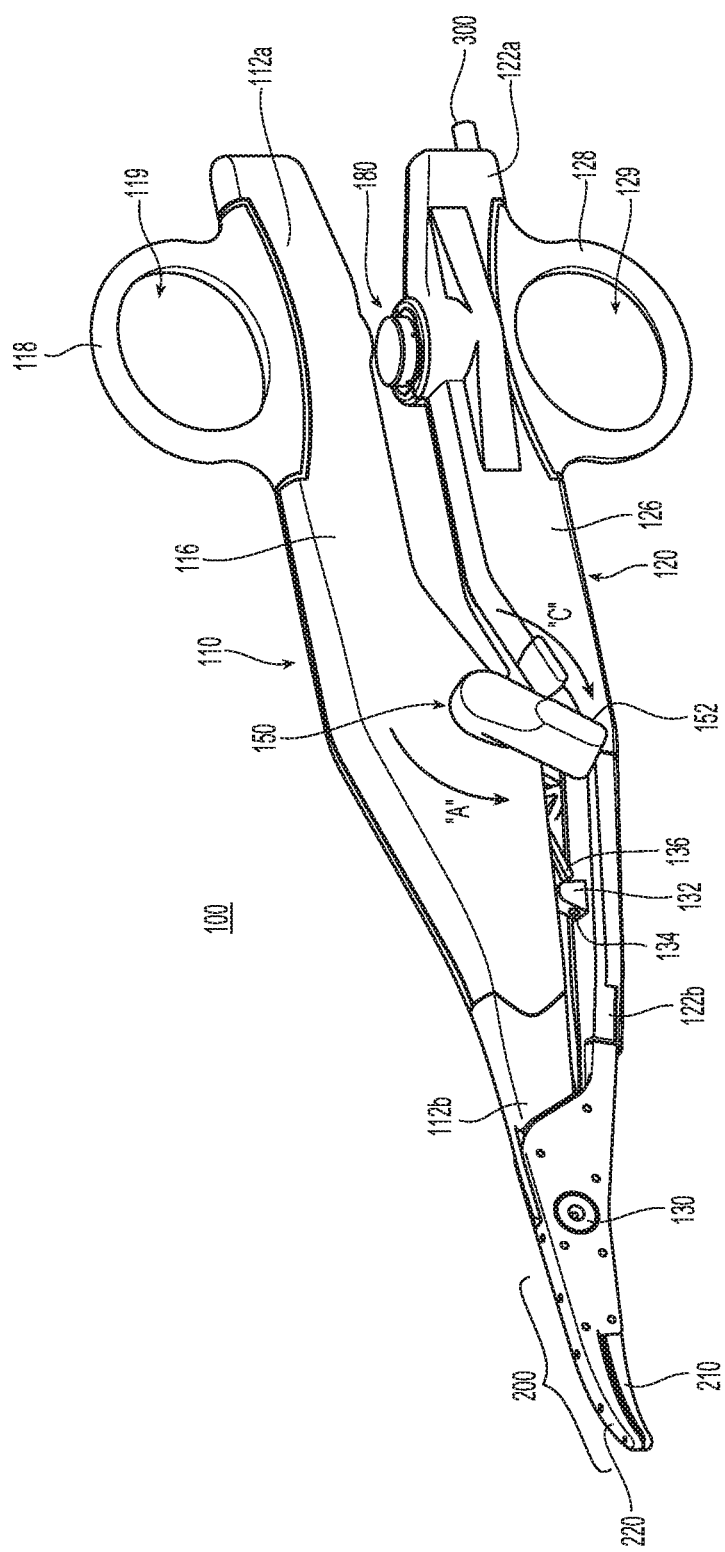
FIG. 1 is a side, perspective view of an electrosurgical forceps provided in accordance with aspects of the present disclosure.
Figure 2:
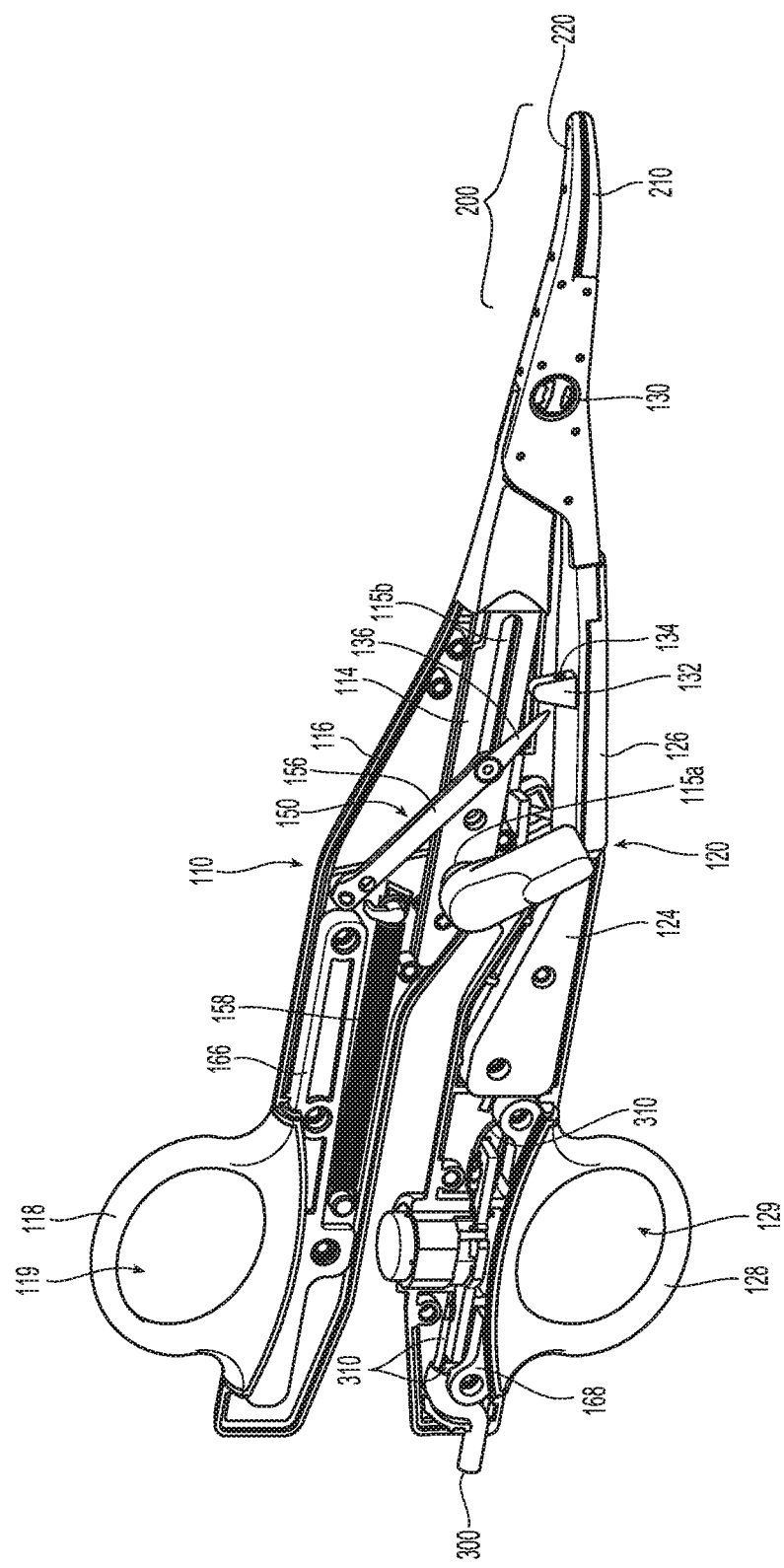
FIG. 2 is a perspective view from one side of the forceps of FIG. 1 with portions of outer housings of first and second shaft members removed to illustrate the internal components therein.

Referring to FIGS. 1 and 2, a forceps 100 provided in accordance with the present disclosure generally includes first and second shaft members 110, 120 and an end effector assembly 200. Shaft members 110, 120 each have a proximal end portion 112a, 122a and a distal end portion 112b, 122b. End effector assembly 200 includes first and second jaw members 210, 220 extending from distal end portions 112b, 122b of first and second shaft members 110, 120, respectively. Forceps 100 further includes a pivot member 130 pivotably coupling first and second shaft members 110, 120 with one another, a knife 140 (FIG. 3), a knife deployment mechanism 150 for selectively deploying knife 140, and a switch assembly 180 for enabling the selective supply of electrosurgical energy to end effector assembly 200. An electrosurgical cable 300 electrically couples forceps 100 to a source of energy (not shown), e.g., an electrosurgical generator, to enable the supply of electrosurgical energy to jaw members 210, 220 of end effector assembly 200 upon activation of switch assembly 180.

Each shaft member 110, 120 includes an inner frame 114, 124, an outer housing 116, 126 surrounding at least a portion of the respective inner frame 114, 124, and a handle 118, 128 engaged with the respective outer housing 116, 126 towards proximal end portions 112a, 122a of first and second shaft members 110, 120, respectively. Inner frame 124 of second shaft member 120 and inner frame 114 of first shaft member 110 are pivotably coupled to one another via pivot member 130 such that shaft members 110, 120 are movable relative to one another between spaced-apart and approximated positions to thereby pivot jaw members 210, 220 relative to one another between open and closed positions.

Outer housings 116, 126 of first and second shaft members 110, 120 enclose and/or operably support the internal components disposed within first and second shaft members 110, 120. More specifically, outer housing 116 of first shaft member 110 encloses and supports at least a portion of inner frame 114 and knife deployment mechanism 150, while outer housing 126 of shaft member 120 receives electrosurgical cable 300 and encloses and supports at least a portion of inner frame 124, switch assembly 180, and the lead wires 310 of electrosurgical cable 300. Handles 118, 128 are engaged with outer housings 116, 126 towards proximal end portions 112a, 112b of first and second shaft members 110, 120 and extend outwardly from first and second shaft members 110, 120. Handles 118, 128 define finger holes 119, 129 configured to facilitate grasping and manipulating shaft members 110, 120.

Second shaft member 120 has a flange 132 extending outwardly therefrom and toward outer housing 116 of first shaft member 110. Flange 132 may be a rectangular-shaped protuberance, or assume any suitable shape, and extend perpendicularly relative to outer housing 126. In some aspects, flange 132 may extend from inner frame 124 of second shaft member 120 or any other stationary component of second shaft member 120, such as outer housing 126 (see FIG. 3.) It is contemplated that flange 132 may be monolithically formed with second shaft member 120 or otherwise mechanically connected thereto. Flange 132 defines a hole 134 (FIG. 5) in a central portion thereof dimensioned to receive of a distal extension 136 of knife deployment mechanism 150, as will be described in more detail below. Hole 134 in flange 132 may be angled such that a proximal entry point of hole 134 is higher than a distal exit point thereof along the path defined therethrough. Angling hole 134 in this manner facilitates the passage of distal extension 136 therethrough. In some aspects, hole 134 may extend only partially through flange 132 so that hole 134 is open only at its proximal entry point. In other aspects, hole 134 may define an arcuate path along which distal extension 136 travels.

Figure 3:
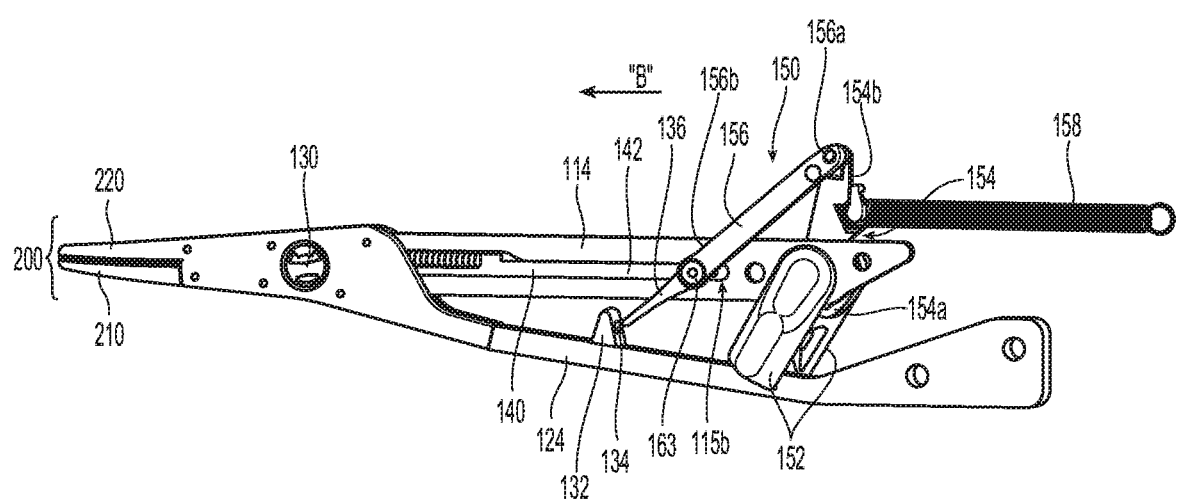
FIG. 3 is a side, perspective view of the forceps of FIG. 1 with portions removed to illustrate a knife and a knife deployment mechanism.

With reference to FIGS. 2 and 3, knife deployment mechanism 150 is coupled to first shaft member 110 and generally includes a pair of opposed triggers 152 extending from either side of first shaft member 110, a crank 154, a linkage 156, and a biasing spring 158. Knife deployment mechanism 150 is disposed within outer housing 116 of first shaft member 110 with the exception of opposed triggers 152, which extend from either side of outer housing 116, and distal extension 136, which will be described in detail below. Crank 154 is configured for positioning on one side of inner frame 114 of shaft member 110 and includes a pair of integral (or otherwise engaged) pivot bosses (not explicitly shown) extending from either side thereof at a first end portion 154a of crank 154. One of the pivot bosses of crank 154 extends through a trigger aperture 115a defined in inner frame 114 (see FIG. 2) and through an aperture (not explicitly shown) defined through a first side of outer housing 116 of first shaft member 110 to enable engagement of one of the triggers 152. The other of the pivot bosses of crank 154 extends through an aperture (not explicitly shown) defined through a second side of outer housing 116 of first shaft member 110 to enable engagement of the other trigger 152 therewith, e.g., via press-fitting, adhesion, or other suitable engagement. As such, rotation of triggers 152 relative to first shaft member 110 drives rotation of crank 154 about first end portion 154a thereof.

Linkage 156 of knife deployment mechanism 150 includes a proximal end portion 156a pivotably coupled to a second end portion 154b of crank 154. A distal end portion 156b of linkage 156 is pivotably coupled to knife 140 via pivot pin 163. Pivot pin 163 may be integrally formed with linkage 156, e.g., as a post extending therefrom, or may be a separate component from linkage 156. Pivot pin 163 extends transversely through a longitudinal slot 115b of inner frame 114 such that pivot pin 163 is constrained to longitudinal movement within longitudinal slot 115b. Linkage 156 is disposed on one side of inner frame 114, which may be the same side as crank 154 or the opposite side (as shown). In either configuration, pivot pin 163 extends from linkage 156 and through longitudinal slot 115b, whereby a portion of pivot pin 163 protrudes laterally from the opposite side of inner frame 114. Knife 140 includes a proximal body 142 through which pin 163 extends transversely to pivotably couple knife 140 to distal end portion 156b of linkage 156.

Biasing spring 158 of knife deployment mechanism 150 may be configured as an extension spring or other suitable biasing spring 158 and is engaged at a distal end portion thereof to crank 154 and at a proximal end portion thereof to a support plate 166. Support plate 166 includes handle 118 of shaft member 110 integrally formed therewith or otherwise engaged thereto, and may be secured within outer housing 116 in any suitable fashion, e.g., via protrusion-aperture engagement. Support plate 166 provides increased structural support to first shaft member 110 to inhibit splaying of first and second shaft members 110, 120 during use. Second shaft member 120 similarly includes a support plate 168 integrally formed with or otherwise engaging handle 128 of shaft member 120 and secured to outer housing 126, although support plate 168 need not extend distally as with support plate 166.

Biasing spring 158 biases crank 154 towards a first orientation, corresponding to the un-actuated position of triggers 152 and the proximal-most position of linkage 156, thereby biasing knife 140 towards the retracted position. Upon rotation of either of triggers 152 relative to first shaft member 110, crank 154 is rotated against the bias of biasing spring 158 to thereby urge linkage 156 distally such that pivot pin 163 is driven distally through longitudinal slot 115b to urge knife 140 from the retracted position towards an extended position, in which knife 140 extends through pivot member 130 and jaw members 210, 220.

Figure 4:
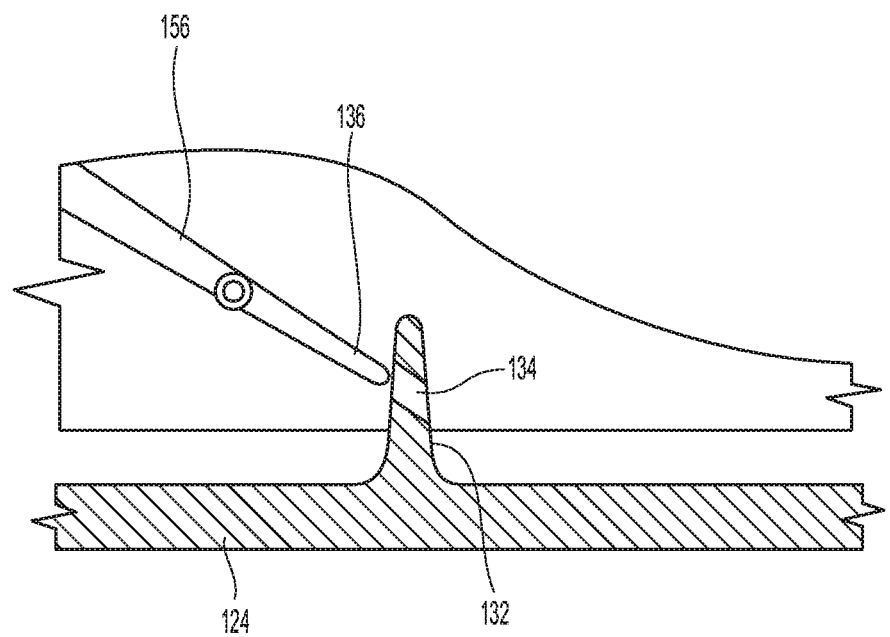
FIG. 4 is a partial side view of the forceps with parts removed to illustrate a lockout mechanism of the forceps.
Figure 5:
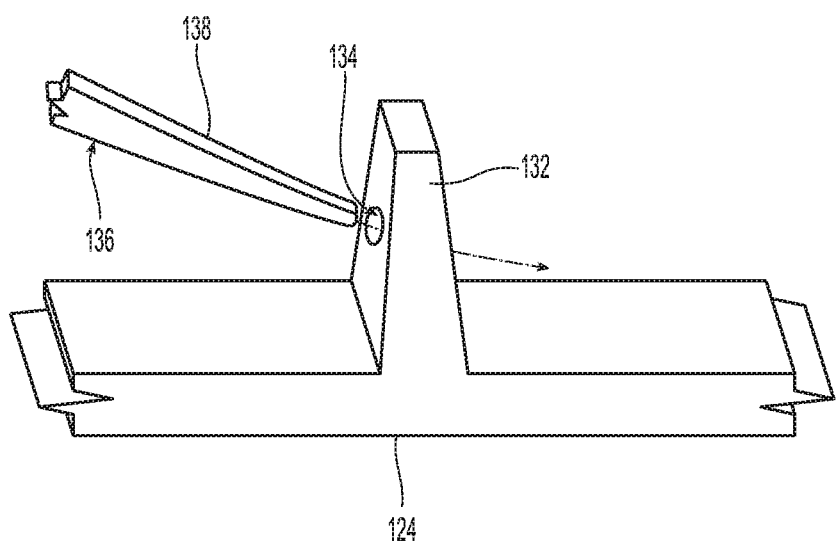
FIG. 5 is an enlarged view of the lockout mechanism of FIG. 4.

With reference to FIGS. 4 and 5, distal extension 136 of knife deployment mechanism 150 is secured to and extends distally from distal end portion 156b of linkage 156. Distal extension 136 is disposed distally of pivot pin 163 and may extend coaxially with linkage 156 or at an angle relative thereto. Distal extension 136 may taper towards its distal end 138 to facilitate passage of distal extension 136 into hole 134 of flange 132 of second shaft member 120. When distal extension 136 is captured in hole 134 of flange 132, separation of first and second shaft members 110, 120 from one another is resisted.

In use, proximal end portions 112a, 122a of first and second shaft members 110, 120 are approximated, thereby moving end effector assembly 200 to the closed configuration. With end effector assembly 200 in the closed configuration, triggers 152 of knife deployment mechanism 150 are actuated (e.g., rotated in the direction indicated by arrow "A" in FIG. 1), which rotates second end portion 154b (FIG. 3) of crank 154 of knife deployment mechanism 150 about first end portion 154a thereof. Rotation of crank 154 rotates and translates linkage 156 of knife deployment mechanism 150. Since pivot pin 163 is supported by distal end portion 156b of linkage 156, pivot pin 163 translates with linkage 156, in the direction indicated by arrow "B" in FIG. 3, to urge the advancement of knife 140 toward the extended position.

While linkage 156 is driven distally, in response to actuation of triggers 152, distal extension 136 approximates flange 132 of second shaft member 120. Upon knife 140 moving to the extended position, distal extension 136 simultaneously passes through hole 134 in flange 132 to lock knife deployment mechanism 150 of first shaft member 110 with second shaft member 120. In this locked state, an attempt at moving proximal end portions 112a, 122a of first and second shaft members 110, 120 away from one another is thwarted by the locked engagement between distal extension 136 and flange 132, and therefore fails to result in the opening of end effector assembly 200. Accordingly, prior to opening end effector assembly 200, distal extension 136 needs to be withdrawn from hole 134 of flange 134 to unlock first and second shaft members 110, 120 from one another.

To unlock first and second shaft members 110, 120, triggers 152 are rotated in the direction indicated by arrow "C" in FIG. 1, which retracts knife 140 out of end effector assembly 200 and simultaneously disengages distal extension 136 from flange 132. In this way, end effector assembly 200 is prevented from being moved from the closed configuration toward the open configuration until knife 140 is moved to the retracted position and out from between first and second jaw members 210, 220.

In one embodiment, flange 132 may be positioned at a location of second shaft member 120 so that flange 132 is distal and adjacent to distal end 138 of distal extension 136 when knife 140 is in the retracted position. In this embodiment, when proximal end portions 112a, 122a of first and second shaft members 110, 120 are spaced relative to one another (i.e., end effector assembly 200 is in the open configuration), distal end 138 of distal extension 136 is blocked from moving distally by flange 132. Given that distal extension 134 is operably coupled to knife 140, preventing advancement of distal extension 136 by flange 132 in turn prevents knife 140 from advancing. Approximating proximal end portions 112a, 122a of first and second shaft members 110, 120 brings distal end 138 of distal extension 136 into alignment with hole 134 in flange 132, allowing distal extension 136 to pass distally therethrough upon actuation of knife deployment mechanism 150, as described above. Accordingly, at least in one embodiment, knife 140 is advanceable from the retracted to the extended position only until after proximal end portions 112a, 122a of first and second shaft members 110, 120 are approximated to bring distal extension 136 into alignment with hole 134 of flange 132.

In yet another aspect of the present disclosure, instead of having a knife safety, forceps 10 may include a trap door (not shown) movably coupled to first shaft member 110. The trap door is disposed in line with the trajectory of knife 140 and blocks the extension of knife 140 when in a first position. Upon closing end effector assembly 200 by approximating proximal end portions 112a, 122a of shaft members 110, 120, second shaft member 120 contacts the trap door, thereby moving the trap door out of the path of the knife 140 to allow for the knife 140 to be selectively deployed.

For additional description of various components and manners of operating forceps 100 of the present disclosure, reference may be made to U.S. patent application Ser. No. 15/593,672, filed on May 12, 2017, the entire contents of which incorporated by reference herein.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

For a detailed description of exemplary medical work stations and/or components thereof, reference may be made to U.S. Patent Application Publication No. 2012/0116416 (now U.S. Pat. No. 8,828,023), and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical forceps, comprising:
a pair of first and second shaft members pivotably coupled to one another, the second shaft member having a flange extending therefrom toward the first shaft member;
an end effector assembly coupled to the pair of first and second shaft members and configured to move between an open configuration and a closed configuration in response to pivoting of the first and second shaft members;
a knife selectively translatable through the first shaft member from a retracted position to an extended position in which the knife extends at least partially through the end effector assembly; and
a knife deployment mechanism coupled to the first shaft member and including a distal extension coupled to the knife, the distal extension configured to move distally toward the end effector assembly and into engagement with the flange of the second shaft member when the knife translates to the extended position and the end effector assembly is in the closed configuration, wherein the engagement between the distal extension and the flange resists movement of the end effector assembly from the closed configuration.

2. The electrosurgical forceps according to claim 1, wherein the knife deployment mechanism includes a linkage operably coupled to the knife configured to move the knife between the retracted and extended positions, the distal extension coupled to and extending distally from a distal end portion of the linkage.

3. The electrosurgical forceps according to claim 2, wherein the knife deployment mechanism includes a pivot pin rotatably supported by the distal end portion of the linkage and coupled to the knife.

4. The electrosurgical forceps according to claim 2, wherein the knife deployment mechanism includes:
a trigger rotatably coupled to the first shaft member; and
a crank having a first end portion coupled to the trigger and a second end portion rotatably coupled to a proximal end portion of the linkage, wherein the knife is configured to move between the retracted and extended positions in response to an actuation of the trigger.

5. The electrosurgical forceps according to claim 4, wherein the crank rotates in response to an actuation of the trigger to rotate and translate the linkage.

6. The electrosurgical forceps according to claim 1, wherein the flange defines a hole dimensioned for receipt of the distal extension.

7. The electrosurgical forceps according to claim 6, wherein the distal extension extends distally through the hole upon the knife moving to the extended position, whereby the hole captures the distal extension and resists the first and second shaft members moving away from one another.

8. An electrosurgical forceps, comprising:
a pair of first and second shaft members pivotably coupled to one another, the second shaft member having a flange extending therefrom toward the first shaft member;
an end effector assembly coupled to the pair of first and second shaft members and configured to transition between an opened configuration and a closed configuration in response to a pivoting of the pair of first and second shaft members;
a knife selectively translatable through the first shaft member from a retracted position to an extended position in which the knife extends at least partially through the end effector assembly; and
a knife deployment mechanism coupled to the first shaft member and including:
a trigger extending from the first shaft member and rotatably coupled thereto;
a linkage operably coupled to the trigger and a proximal end portion of the knife; and
a distal extension coupled to a distal end portion of the linkage and configured to engage the flange of the second shaft member when the knife is in the extended position, wherein the engagement between the linkage and the flange resists movement of the first and second shaft members away from one another, wherein the flange of the second shaft member is positioned distal of and aligned with the distal extension when the end effector assembly is in the opened configuration to prevent the knife from translating toward the extended position.

9. The electrosurgical forceps according to claim 8, wherein the knife deployment mechanism includes a crank having a first end portion coupled to the trigger and a second end portion operably coupled to a proximal end portion of the linkage.

10. The electrosurgical forceps according to claim 8, wherein the end effector assembly includes:
   a first jaw member coupled to and extending distally from the first shaft member; and
   a second jaw member coupled to and extending distally from the second shaft member.

11. The electrosurgical forceps according to claim 10, wherein the engagement between the linkage and the flange resists movement of the first and second jaw members from the closed configuration.

12. The electrosurgical forceps according to claim 8, wherein the flange defines a hole dimensioned for receipt of the distal extension.

13. The electrosurgical forceps according to claim 12, wherein the distal extension extends through the hole upon the knife moving to the extended position, whereby the hole captures the distal extension and resists the first and second shaft members moving away from one another.

14. The electrosurgical forceps according to claim 8, wherein the knife deployment mechanism includes a pivot pin rotatably supported by the distal end portion of the linkage and coupled to the knife.

\* \* \* \* \*